United States Patent
Li et al.

(10) Patent No.: US 9,605,247 B2
(45) Date of Patent: Mar. 28, 2017

(54) STRAIN AND A METHOD TO PRODUCE CELLULASE AND ITS USE

(71) Applicant: Hunan Hongying Biotechnology Co., Ltd, Jinshi, Hunan Province (CN)

(72) Inventors: Hongbing Li, Jiashi (CN); Haiqing Li, Jiashi (CN); Jinjie Zhang, Jiashi (CN); Yongming Zhu, Jinshi (CN)

(73) Assignee: HUNAN HONG YING BIOTECH CO., LTD., Jinshi Hunan (CN)

( * ) Notice: Subject to any disclaimer, the term of this patent is extended or adjusted under 35 U.S.C. 154(b) by 0 days.

(21) Appl. No.: 14/578,408

(22) Filed: Dec. 20, 2014

(65) Prior Publication Data
US 2015/0175988 A1    Jun. 25, 2015

(30) Foreign Application Priority Data

Dec. 23, 2013   (CN) .......................... 2013 1 0716663
Dec. 23, 2013   (CN) .......................... 2013 1 0716678

(51) Int. Cl.
*C12N 9/42*   (2006.01)
*C12N 1/14*   (2006.01)

(52) U.S. Cl.
CPC ............. *C12N 9/2437* (2013.01); *C12N 1/14* (2013.01)

(58) Field of Classification Search
None
See application file for complete search history.

(56) References Cited

FOREIGN PATENT DOCUMENTS

| CN | 101735993 | * | 6/2010 |
| CN | 201010040047.2 A | | 6/2010 |
| CN | 201310268728.8 A | | 9/2013 |

OTHER PUBLICATIONS http://www.atcc.org/products/all/56764.aspx#history, accessed Apr. 1, 2016.*

* cited by examiner

*Primary Examiner* — Erin M Bowers
(74) *Attorney, Agent, or Firm* — Michael Ye; Andrews Kurth Kenyon LLP

(57) ABSTRACT

The present invention relates to a mutant strain of *Trichodema reesei*, namely, CCTCC No: M 2013540, that produces cellulase with high enzyme activity, and a method of producing thereof. The enzyme activity of the cellulase was as follows: Filter Paper Activity (FPA):792 U/mL, Endo-1, 4-β-D-glucanase (EG):1389 U/mL, Exo-1, 4-β-D-glucannase (CBH):680 U/mL, β-1, 4-glucosidase (BG):486 U/mL.

4 Claims, No Drawings

STRAIN AND A METHOD TO PRODUCE CELLULASE AND ITS USE

CROSS-REFERENCE TO RELATED APPLICATION

This application claims the priority of two Chinese Patent Applications No. CN2013107166639, filed on Dec. 23, 2013, and CN2013107166785, filed on Dec. 23, 2013. The content of both is incorporated herein by reference.

BACKGROUND

Technical Field

The present invention relates to a novel strain of *Trichoderma* which can produce cellulase and a method for producing the cellulase therefrom.

Background Art

Cellulase exists widely in various organisms in the nature. It could be produced from bacteria, fungi and animal body. Generally, cellulase used for industrial production is prepared from fungi, typically *Trichoderma* (*Trichodema*), *Aspergillus* (*Aspergillus*), and *Penicillium* (*Penicillium*) fermentation. The cellulase is applied in a food industry and an environmental industry extensively.

Filamentous fungi of phylum (division) Ascomycota, including various *Penicillium, Phanerochaete, Agaricus, Neurospora, Humicola, Fusarium, Chaetomium, Magnaporthe, Aspergillus* and *Trichoderma* species, have a key role in degradation of most abundant polymers found in nature. *Trichoderma reesei* (the asexual anamorph of *Hypocrea jecorina*) is an important industrial source of cellulase and hemicellulase enzymes. The term cellulase (or cellulase enzymes) broadly refers to enzymes that catalyze the hydrolysis of beta-1,4-glucosidic bonds joining individual glucose units in cellulose polymers. Its catalytic mechanism involves synergistic actions of endoglucanases (E.C. 3.2.1.4), cellobiohydrolases (E.C. 3.2.1.91) and beta-glucosidase (E.C. 3.2.1.21). The term hemicellulase broadly refers to enzymes that catalyze the hydrolysis of various glycosidic bonds joinings.

A cellulase system consists of three major components according to their differences in catalytic functions: Endoglucanases (endo-1,4-β-D-glucanases or 1,4-β-D-glucan glucanohydrolase; EC 3.2.1.4, C1, EG and CEN derived from fungi and bacteria individually), cellobiohydrolases (exo-1,4-β-D-glucanases or 1,4-β-D-glucan cellobilhydrolase; EC 3.2.1.91; Cx, CBH and Cex derived from fungi and bacteria individually), and β-glucosidases (1,4-β-D-glucosidase; βG; BGL, EC 3.2.1.21). The EG acts on insoluble cellulose surfaces, breaks internal bonds to disrupt crystalline structures of the cellulose and expose individual cellulose polysaccharide chains, and makes hydration of the cellulose chains easily. The CBH cleaves 2-4 units from ends of the exposed chains produced by the EG, resulting in tetrasaccharides or disaccharide such as cellobiose. There are two main types of the CBH a first type working processively from a reducing end, and a second type working processively from a non-reducing end of the cellulose. The βG hydrolyses CBH products into individual monosaccharides. Through synergistic actions of the above enzyme system, the cellulose can be efficiently hydrolyzed to glucose.

The cellulase's enzymatic reaction is different from general enzymatic catalytic reactions, lying in that the cellulase is a multicomponent enzyme system, and the structures of its substrates are extremely complex. Because of the insolubility of the substrates, an ES formation process in general enzymatic reaction could not be accomplished. Instead, the adsorption prosperity of the cellulase makes it adhering to the cellulose substrate. and the celluase catalyzes the cellulose into the glucose under the synergistic actions of several components of the cellulase.

In 1950, Reese et. al proposed a C1-Cx hypothesis, which stated that a different enzyme synergistic effect for hydrolyzing cellulose completely into the glucose. A synergistic effect is generally considered that a endoglucanase (C1 enzyme) amorphous region first attack ingcellulose, the formation of Cx required a new free end, and then by the Cx enzyme from the reducing end of polysaccharide chains or non reducing end cutting fiber into two sugar units, and finally by the beta glucanase will hydrolyze them into two glucose. However, the sequential collaborative effect of the cellulase is not absolute. Found in subsequent research, C1-Cx and beta glucanase must all be present to hydrolyze natural cellulose. If t C1 enzyme was added first to act on crystalline cellulose, then replaced with Cx enzyme, the crystalline cellulose could not be hydrolyzed.

Breeding is a foundation of cellulase production domestic and foreign experts have done a lot of research on productions of the cellulase products with high quality. For example, Wang Jialin (1996), has introduced *Trichoderma* 10, *Trichoderma viride* Sn-91014, *Trichoderma koningii* NT-15, *Aspergillus niger* XX-15A. From them, Wang obtained high yield strain NT15-H, NT15-H1, XT-15H, XT-15H1 by using ultraviolet radiation, specific electromagnetic wave radiation, linear accelerator, and NTG mutagenesis method of physics and chemistry. The *Trichoderma* NT-15H solid culture activity by the Ministry of light industry food quality supervision and testing center of NanJing Railway Station detection showed that filter paper enzyme activity was 3670 u/g, C1-, 24460 u/g enzyme activity, Cx-enzyme activity of 1800 u/g, has reached an international superior level. The strains maintain stable qualities in industrial production. Zhang Linghua (1998) selected *Trichoderma koningii* W-925, J-931, which were induced mutations by 2% diethyl sulfate and ultraviolet (15W, 30 cm, 2 min) inductions, to produce high enzyme activity of Wu-932 strain. said strain has CMC saccharification enzyme activity of 2975 and 531, which equaled to 100% and 81% increase from that of strain W-925. Wang Chengshu from Department of chemical feed additive technology service center (1997) mutated *Trichoderma reesei* A3 by UV and NTG treatments. The spores were inoculated in a fiber double plate for 5-8 days at 30° C., then 7-10 days at 15° C. Single colonies having transparent circles and large diameters were selected and transferred to flasks for a solid-state fermentation screening. *Trichoderma reesei* strain 91-3 with very high cellulase activity was obtained.

There are two main kinds of production technologies of the cellulase, namely solid fermentation and liquid fermentation, the process is as follows:

Various factors could affect the yield of enzyme and its activity, including microbe species, culture temperature, pH, moisture, substrate, and cultivation time. These factors are not independent but interrelated. Adopting uniform design method C112 (1210) and *Trichoderma viride* (T.ViriclePers.expr) as strain, Zhang Zhongliang (1997) investigated the effect of five major factors on the production of the cellulase and its enzymatic activity. Zhang found that the culture conditions of 40% matrix crude fiber content, at initial pH7.5, with 4 times of water, at a temperature of 26-31° C. for 45 h would provide the maximum yield of enzyme of 26 mg/g and CMC enzyme activity of 20 mg/g·h$^{-1}$. Wang Chenghua (1997) has also studied *Trichoderma reesei* 91-3 enzyme producing condition. His results showed that the strain 91-3 fermented best in a medium composed of a mixture of 7:3 of straw powder and wheat bran, with 4% ammonium sulfate, 0.4% potassium dihydrogen phosphate, and 0.1% magnesium , at 28-32° C. or preferably at 30° C. for 96 h. Zhang Linghua (1998) studied optimal fermentation conditions of mutated Wu-932 cellulase producing strains of *Trichoderma koningii* W-925 as starting strain,. The results showed that, a ratio of 1:2 of wheat bran and rice straw powder medium, an inoculation amount of 5%, an average length of 3-5 mm of straws, an initial pH4-5, a temperature of 28-35° C., and a fermentation time of 72 h were the optimal fermentation conditions.

A preparation method of the cellulase was mentioned in CN201010040047 by Zhejiang University, which contains following steps: Ricem (*Trichderma reesei*) were inoculated into a fermentation medium with a fed-batch culture pattern, wherein the fermentation medium was fed to the fermentation system when the pH of the fermented broth is higher than 4.8 , and the feeding was stopped when the pH was lower than 4.5; the total fermentation time was extended to 192-240 hours. Moreover, said invention introduced a combination of an insoluble and a soluble carbon sources to induce an expression of cellulase genes. The balance in microbe growth and metabolite production is maintained through fed batch culture, which solved problems when cellulose or soluble sugar was used as inducers for the cellulase production, effectively improving the level of cellulase fermentation.

A preparation method of a low-temperature neutral cellulase was invented as CN2013102687288. *Trichoderma reesei* was used to produce the cellulase through of a serial of steps: the seed was activated, UV mutagenesised, cultured at low temperature and purified; then, a resulting seed solution was inoculated to a producing-medium, cultured for 96-144 hours at 10-15° C. for the cellulase production. The invention also provides a method of compounding the low-temperature neutral cellulase. The beneficial effects of the invention were: simple operation, short fermentation cycle, reduction of the temperature of the application of enzyme, leading to reduction of the power consumption of industrial applications, which make it more environmentally friendly, and has wide application prospect.

DESCRIPTION OF THE INVENTION

One objective of the present invention is to provide a mutant strain of *Trichoderma* and a method for producing cellulase with high enzyme activity and its use.

According to one embodiment of the present invention, the strain can be used to produce the cellulase, wherein the strain *Trichoderma reesei* has been deposited in CCTCC with the accession number CCTCC No: M 2013540.

CCTCC No: M 2013540 has been deposited in China Center for Type Culture Collection (CCTCC; College of Life Sciences, Wuhan University, Wuhan 430072, P. R. China) on Nov. 3, 2013, and its classification name is *Trichoderma reesei* 601-17. The strain was deposited at CCTCC under the Budapest Treaty and will be made available to the public upon issuance of a patent.

An optimum pH and an optimum temperature for *Trichoderma reesei* 601-17's cellulase production is 3.0-6.0, and 23~35° C., respectively.

The enzyme activity of the cellulase which was obtained from fermentation by the strain of *Trichoderma reesei* 601-17 was as follows:

Filter Paper Activity (FPA): 792 U/mL.
Endo-1,4-β-D-glucanase (EG): 1389 U/mL.
Exo-1,4-β-D-glucannase (CBH): 680 U/mL.
β-1,4-glucosidase (BG): 486 U/mL.

The steps of the cellulase production is as follows:
transferring the strain of *Trichodema reesei* CCTCC No: M 2013540 into a fermentation medium;
cultivating said strain into a seed fermentation broth, wherein a cultivating time is 72-96 h;
transferring the seed fermentation broth to a fermentation medium, wherein the seed fermentation broth consists 5-10% of the volume of the fermentation medium;
fermenting said fermentation medium at a temperature between 20-35° C., for a time between 96-144 h;
collecting a supernatant fluid by centrifuging at a speed between 4000-6000 rpm; and,
preparing a concentrated enzyme broth of the cellulose by ultra-filtrating of said supernatant fluid the fermentation broth.

Enzyme assay methods are the same as those disclosed in 《Ferment conditions optimizing for producing cellulase and cloning of CBH1 of Penjcillium oxalicun Currie & Thom》 (Zhang Qian,2009).

The mycologic properties of the *Trichoderma reesei* CCTCC NO: M 2013540 are described below:

[Morphological Properties]

Aerial myceliums: white at the initial stage, and grew as radiating pattern.

Conidiophores: the conidiophores could arise from mycelia, tips of the conidiophores are swollen to form pear-shaped acrocysts ,and release conidia.

Spores: green, spherical, smooth, with a diameter of 20-100 μm.

[Culture Properties]

The strain can be cultivated on PDA medium. Its colony is of light green color and batt-like looking. The colony is flat, its height is 0.1-0.75 mm, its edge is white. The scale of the colony is about 1~8.5 mm after 48 hours of cultivating, and 30~50 mm after 72 hours of cultivating, wherein its surface is smooth with neat edge,

[Fermentation Method]

The strain's fermentation method to produce the cellulase is the same as those for other *Trichoderma reesei*. Cultivate *Trichoderma reesei* is inoculated from a slant medium to a flask or a fermentator. The inoculation quantity is controlled at 5% of the total volume of medium in the flask or the fermentator. Said inoculation step may be repeated until a desired volume of the seed fermentation broth is obtained. A time period for preparing the seed fermentation broth is around one to four days. The seed fermentation broth is inoculated in the fermentation medium and then incubated at 25-37° C. for 96-144 hours before the fermentation is finished. Then the supernatant fluid is collected by filtrating or centrifuging. The concentrated enzyme solution could be prepared after the ultra-filtration or other methods.

[Physiological Properties]

A viable pH ranges between 3.0-6.0, Furthermore , the grows temperature ranges between 23-35° C.

The strain could grow on a bran, and its main metabolite is cellulases(endo-1,4-β-D-glucanase(EG) ,exo-1,4-β-D-glucannase (CBH), β-1,4-glucosidase (BG)). According to 《An Introduction industrial mycology》 (George Smith 1954), 《Fungal identification manual》 (Wei Jingchao 1982), 《Common fungi》 (The Chinese academy of sciences institute of microbiology 1973), the organism was identified as *Trichoderma reesei*.

The present invention will be hereafter described in detail with reference to the following embodiments. However the technical scope of the present invention is not limited thereto.

Embodiment 1

Isolation and Mutation

An original strain (*trichodema reesei*) hyx01 was isolated from a field located in a mushroom plantation in the city of Jinshi in Hunan province in China. The original strain was cultivated to collect spore suspension. Then, the spore suspension was exposed to ultraviolet light. Then, the spore suspension was diluted with sterile water, wherein the spores in the suspension are $10^8$ /mL. Then the diluted spore suspension was spread to a selection medium which contains cellulose and congo red. Then the selection medium with the spores was cultivated at 30° C. for 3 days. Then the strain's colonies having large volume and transparent circle were selected. 200 of said colonies were picked and kept in the slant medium.

The selection medium was composed of (g/L): cellulose powder 10, congo red 0.2, ammonium sulfate 5, magnesium sulfate 0.25, potassium dihydrogen phosphate 1, sodium chloride 0.1, gelatin 2. All components described immediately above were dissolved in water, which is then adjusted to PH 5-6 and autoclaved at 121° C. for 20 minutes.

The original strains were transferred to the slant medium and were cultured until their spores were full of slant medium. The spores were washed with the sterile water and transferred to a flask of 250 ml with a medium in it and fermented for 96 hours at 30° C., with a rotation speed of 100 rpm. Then the enzyme activity was measured.

The medium was a water solution composed of (per L): 50 g cellulose, 5 g ammonium sulfate, 0.25 g magnesium sulfate, 1 g monopotassium phosphate, 0.1 g sodium chloride, at pH 5-6.

The strain *Trichodema reesei* 601-17 which had the highest cellulase activity was selected.

A suitable pH for the strain *Trichodema reesei* 601-17 to produce the cellulase was 3.0-6.0 ; a suitable temperature for the strain *Trichodema reesei* 601-17 to produce the cellulase was 27~30 ° C.

Genetic stability experiment of *Trichodema reesei* 601-17.

The strain 601-17 was transferred for ten generations on the slant mediums. The fermentation was carried out with each generation of said strain 601-17. Enzyme activities were measured for all generation. Results shows that characteristic of each generation strain was the same and as well for the enzyme activities of said strain. The result showed that the strain 601-17 maintained good genetic stability.

Fermentation in Large Scale

The strain 601-17 was transferred into a flask of 500 ml with 100 ML of the seed medium, and fermented at 30° C. for 72-96 hours, with an agitation speed of 150 rpm. The seed fermentation broth was transferred into a fermentor of 10 L with 7.5 L of the fermentation medium, and fermented at 27° C. for 104 hours, with a rotation speed of 300 rpm, at an air flow rate (v/v) of 1:0.8-1.2 and a pH of 5.0±0.2, and at a dissolved oxygen concentration of 20-30% by adjusting the rotation speed and aeration ratio.

After fermentation, the supernatant fluid was collected by the filtration or the centrifugation. The cellulase activity in the supernatant fluid was measured as bellow:
Filter Paper Activity (FPA): 792 U/mL.
Endo-1,4-β-D-glucanase (EG): 1389 U/mL.
Exo-1,4-β-D-glucannase (CBH): 680 U/mL.
β-1,4-glucosidase (BG): 486 U/mL.

The Seed medium was a water-solution composed of (per L): 50 g cellulose, 3 g ammonium sulfate, 0.25 g magnesium sulfate, 1 g monopotassium phosphate, 0.1 g sodium chloride, pH 5-6.

The fermentation medium was a water-solution composed of (per L); 10 g cellulose, 5 g ammonium sulfate,0.25 g magnesium sulfate, 1 g monopotassium phosphate, 0.1 g sodium chloride, pH 5-6.

The strain of *Trichodema reesei* CCTCC No: M 2013540 can be kept for 32 months at 4° C. with the slant medium. CCTCC No: M 2013540 can be kept for many years in a solution containing 15-25 percent of glycerol or sorbierite under a temperature of 78~80 ° C. below 0° C.

The Slant medium is composed of: 20% potato, 1% glucose, 2% agar. Natural pH.

Embodiment 2

Cellulase Production

The Seed fermentation broth of CCTCC No: M 2013540 was transferred into the fermentor of 10 L with 7.5 L of the fermentation medium. The fermentation time was 104 h at the temperature of 27° C., the agitation speed of 300 rpm, The air flow rate (v/v) of 1:1.2, the pH of 5.0±0.2, and the dissolved oxygen concentration is maintained at 25% by adjusting the rotation speed and the aeration ratio, After the fermentation, the supernatant fluid was collected from fermentation broth by the filtration or the centrifugation. The cellulase activity in the supernatant fluid was measured as bellow:
Filter Paper Activity (FPA): 792 U/mL.
Endo-1,4-β-D-glucanase (EG): 1389 U/mL.
Exo-1,4-β-D-glucannase (CBH): 680 U/mL.
β-1,4-glucosidase (BG):486 U/mL.

The fermentation medium was composed of (per L); 10 g cellulose, 5 g ammonium sulfate,0.25 g magnesium sulfate, 1 g monopotassium phosphate, 0.1 g sodium chloride, pH 5-6.

We claim:

1. A mutant Trichoderma strain for production of cellulase, wherein the strain is Trichoderma reesei 601-17 with a preservation number CCTCC No: M 2013540.

2. The strain of claim 1, characterized in that, the strain has physiological-biochemical characteristics as follows:
   the strain grows on a PDA solid medium and forms gossypine, and flat colonies, with a height of 0.1 to 0.75 mm, as well as a white edge;
   the hyphae are white, and have septa and smooth hyphal walls, with a diameter of 2 to 5 µm;
   conidiophores grow from lateral branches of the hyphae, and occur in pairs on the lateral branches; the conidiophores are bottle-shaped, upright, and colorless, and spores are sphere-shaped and green, with a diameter of 20-100 µm.

3. The strain of claim 1, characterized in that, the cellulase produced by the strain has optimum pH of 3.0 to 6.0, and optimum temperature of 23 to 35° C.

4. The strain of claim 2, characterized in that, the cellulase produced by the strain has optimum pH of 3.0 to 6.0, and optimum temperature of 23 to 35° C.

* * * * *